United States Patent
Crabtree

(10) Patent No.: US 8,043,368 B2
(45) Date of Patent: Oct. 25, 2011

(54) METHODS AND APPARATUS FOR ATRIOVENTRICULAR VALVE REPAIR

(76) Inventor: Traves Dean Crabtree, Glen Carbon, IL (US)

(*) Notice: Subject to any disclaimer, the term of this patent is extended or adjusted under 35 U.S.C. 154(b) by 435 days.

(21) Appl. No.: 11/287,011

(22) Filed: Nov. 23, 2005

(65) Prior Publication Data

US 2007/0118154 A1    May 24, 2007

(51) Int. Cl.
| | |
|---|---|
| A61F 2/24 | (2006.01) |
| A61F 2/02 | (2006.01) |
| A61F 13/00 | (2006.01) |
| A61F 2/00 | (2006.01) |
| A61B 19/00 | (2006.01) |
| A61B 17/10 | (2006.01) |
| A61B 17/04 | (2006.01) |
| A61B 17/12 | (2006.01) |
| A61B 17/08 | (2006.01) |
| A61D 1/00 | (2006.01) |

(52) U.S. Cl. ............ 623/2.11; 623/2.1; 623/23.72; 128/898; 600/37; 606/151; 606/139; 606/144; 606/213; 606/232; 606/142

(58) Field of Classification Search ........... 606/151, 606/139, 144, 213, 232, 142; 623/2.1, 2.11, 623/23.72; 600/37; 128/898
See application file for complete search history.

(56) References Cited

U.S. PATENT DOCUMENTS

| | | | |
|---|---|---|---|
| 6,629,534 B1* | 10/2003 | St. Goar et al. ........... 128/898 |
| 7,144,363 B2* | 12/2006 | Pai et al. ............ 600/16 |
| 7,635,386 B1* | 12/2009 | Gammie ............ 623/2.11 |
| 2003/0078465 A1* | 4/2003 | Pai et al. ............ 600/16 |
| 2003/0078653 A1* | 4/2003 | Vesely et al. ............ 623/2.16 |
| 2003/0105519 A1* | 6/2003 | Fasol et al. ............ 623/2.1 |
| 2003/0120341 A1* | 6/2003 | Shennib et al. ............ 623/2.12 |
| 2004/0193191 A1* | 9/2004 | Starksen et al. ............ 606/153 |
| 2005/0070999 A1* | 3/2005 | Spence ............ 623/2.37 |
| 2005/0075727 A1 | 4/2005 | Wheatley |
| 2005/0125011 A1 | 6/2005 | Spence et al. |
| 2005/0240202 A1 | 10/2005 | Shennib et al. |
| 2007/0118213 A1* | 5/2007 | Loulmet ............ 623/2.1 |
| 2008/0228272 A1* | 9/2008 | Moaddeb et al. ............ 623/13.13 |
| 2010/0023118 A1* | 1/2010 | Medlock et al. ............ 623/2.11 |

FOREIGN PATENT DOCUMENTS

| | | |
|---|---|---|
| WO | 9911201 A2 | 3/1999 |
| WO | 9930647 A1 | 6/1999 |
| WO | 0230295 A1 | 4/2002 |
| WO | 2006041877 A2 | 4/2006 |
| WO | 2007061834 A2 | 5/2007 |
| WO | 2007062054 A2 | 5/2007 |

OTHER PUBLICATIONS

PCT International Search Report and Written Opinion, Int'l. App. No. PCT/US06/45217 (Aug. 6, 2007).
EP Supplementary Search Report PCT/US2006045217 dated Dec. 9, 2010, 8 pages.

* cited by examiner

*Primary Examiner* — Thomas J Sweet
*Assistant Examiner* — Jacqueline Woznicki
(74) *Attorney, Agent, or Firm* — Armstrong Teasdale LLP

(57) ABSTRACT

Methods and apparatus for use in repairing an atrioventricular valve in a patient are provided. The methods comprise accessing the patient's atrioventricular valve percutaneously, securing a fastening mechanism to a valve leaflet, and coupling the valve leaflet, while the patient's heart remains beating, to at least one of a ventricular wall adjacent the atrioventricular valve, a papillary muscle, at least one valve chordae, and a valve annulus to facilitate reducing leakage through the valve.

27 Claims, 8 Drawing Sheets

US 8,043,368 B2

METHODS AND APPARATUS FOR ATRIOVENTRICULAR VALVE REPAIR

BACKGROUND OF THE INVENTION

This invention relates generally to medical methods and apparatus, and more particularly, to methods and apparatus for the endovascular or minimally invasive surgical repair of atrioventricular valves of the heart, including the mitral valve and the tricuspid valve.

The heart includes four valves that direct blood through the two sides of the heart. The mitral valve lies between the left atrium and the left ventricle and controls the flow of blood into the left side of the heart. The valve includes two leaflets, an anterior leaflet and a posterior leaflet, that close during systole. The leaflets are passive in that they open and close in response to pressure induced to the leaflets by the pumping of the heart. More specifically, during a normal cycle of heart contraction (systole), the mitral valve functions as a check valve to prevent the flow of oxygenated blood back into the left atrium. In this manner, oxygenated blood is pumped into the aorta through the aortic valve.

Occasionally, the mitral valve is formed abnormally through a congenital condition. More often, however, the mitral valve degenerates with age. Among the problems that can develop is mitral valve regurgitation in which the mitral valve leaflets become unable to close properly during systole, thus enabling leakage to flow through the mitral valve during systole. Over time, regurgitation of the mitral valve can adversely affect cardiac function and may compromise a patient's quality of life and/or life-span.

Mitral valve regurgitation can result from a number of different mechanical defects in the mitral valve. For example, the valve leaflets, the valve chordae which connect the leaflets to the papillary muscles, or the papillary muscles themselves may become damaged or otherwise dysfunctional. Moreover, the valve annulus may become damaged or weakened and may limit the ability of the mitral valve to close adequately during systole.

Known treatments for mitral valve regurgitation commonly rely on valve replacement or annuloplasty, or strengthening of the mitral valve through surgical repairs and/or implanting a mechanical structure within the mitral valve. For example, the most prevalent and widely accepted known techniques to correct mitral valve regurgitation, repair the mitral valve via open heart surgery. During such an invasive surgical procedure, it is known to suture adjacent segments of the opposed valve leaflets together in a procedure known as a "bow-tie" or "edge-to-edge" surgical technique. Although each of the afore-mentioned treatments can be effective, generally known treatments rely on open heart surgery wherein the patient's chest is opened and the patient's heart is stopped while the patient is place on a cardiopulmonary bypass. The need to open the patient's chest and to place the patient on a cardiopulmonary bypass creates inherent risks that may be traumatic to the patient.

Percutaneously treatments are less invasive than the treatments mentioned above, but such treatments may be less effective and more difficult to effect repair because of the limited amount of space in and around the mitral valve in which to maneuver a repair device or devices. For example, U.S. Pat. No. 6,875,224 to Grimes describes a percutaneous mitral valve repair method in which the opposed leaflets are each immobilized to enable the two leaflets to be fastened together. Furthermore, U.S. Pat. No. 6,6290,534 to St. Goar et al. describes a plurality of embodiments for use in endovascular repair of cardiac valves in which, in each embodiment, both leaflets are grasped and held firmly in position prior to permanent treatment. However, grasping both leaflets while the patient's heart is beating may be a time-consuming and laborious task that demands a coordinated effort on the part of the surgical team. Moreover, to facilitate grasping both leaflets percutaneously may require that the patient's heart be temporarily stopped or slowed by drugs or other techniques. Slowing and/or stopping the patient's heart during surgery may increase the risks to the patient.

BRIEF DESCRIPTION OF THE INVENTION

In one aspect, a method of repairing an atrioventricular valve in a patient is provided. The method comprises accessing the patient's atrioventricular valve percutaneously, securing a fastening mechanism to a valve leaflet, and coupling the valve leaflet, while the patient's heart remains beating, to at least one of a ventricular wall adjacent the atrioventricular valve, a papillary muscle, at least one valve chordae, and a valve annulus to facilitate reducing leakage through the valve.

In another aspect, a method of repairing a mitral valve in the heart of a patient is provided. The method comprises accessing the patient's mitral valve percutaneously, securing a first end of a fastening mechanism to a valve leaflet of the mitral valve, and coupling a second end of the fastening mechanism to a cardiac structure other than a mitral valve leaflet to facilitate reducing leakage through the patient's mitral valve during ventricular systole.

In a further aspect, a method of enhancing operation of a patient's heart valve is provided. The method comprises inserting a guide catheter along the venous system of the patient to approach the mitral valve, guiding a fastening mechanism towards one of a mitral valve and a tricuspid valve within the patient's heart, and securing a first end of the fastening mechanism to one of the mitral valve and the tricuspid valve using one of fusing, gluing, stapling, clipping, riveting, anchoring, and suturing. The method also comprises securing a second end of the fastening mechanism to a cardiac structure other than a valve leaflet to facilitate enhancing operation of the valve during ventricular systole.

In an additional aspect, a medical kit for use in repairing a mitral valve is provided. The kit includes a guide catheter and a fastening mechanism. The guide catheter is configured for insertion along the venous system of the patient to approach the mitral valve. The fastening mechanism is positionable percutaneously within the patient using the guide catheter. The fastening mechanism includes a first end and an opposite second end. The first end is configured to couple to the mitral valve using one of fusing, gluing, stapling, clipping, riveting, anchoring, and suturing. The second end is configured to only couple to a cardiac structure other than a valve leaflet to facilitate enhancing operation of the valve during ventricular systole.

DETAILED DESCRIPTION OF THE INVENTION

Figure 1:
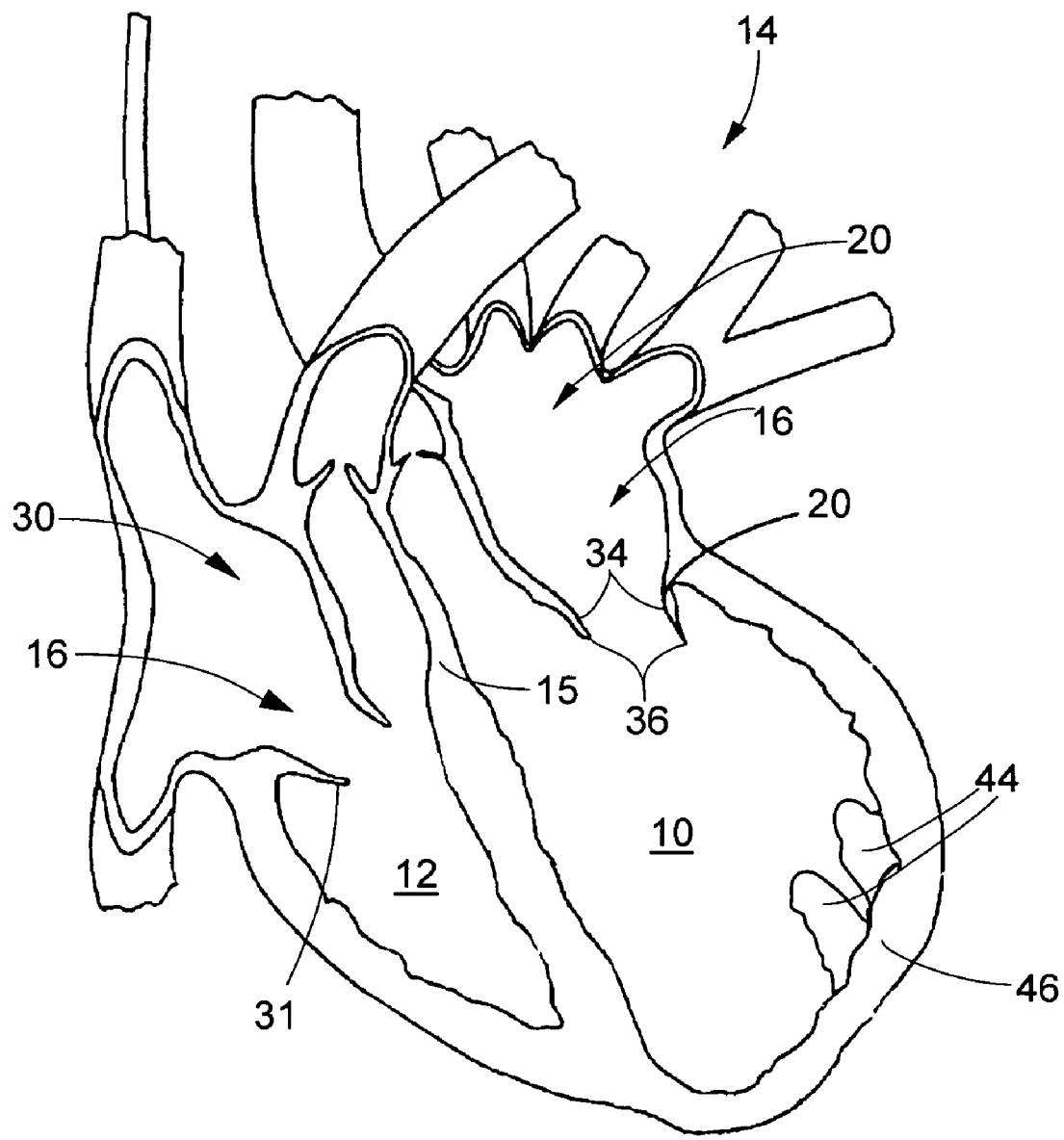
FIG. 1 is a cross-sectional view of the left and right ventricles of a human heart in diastole.
Figure 2:
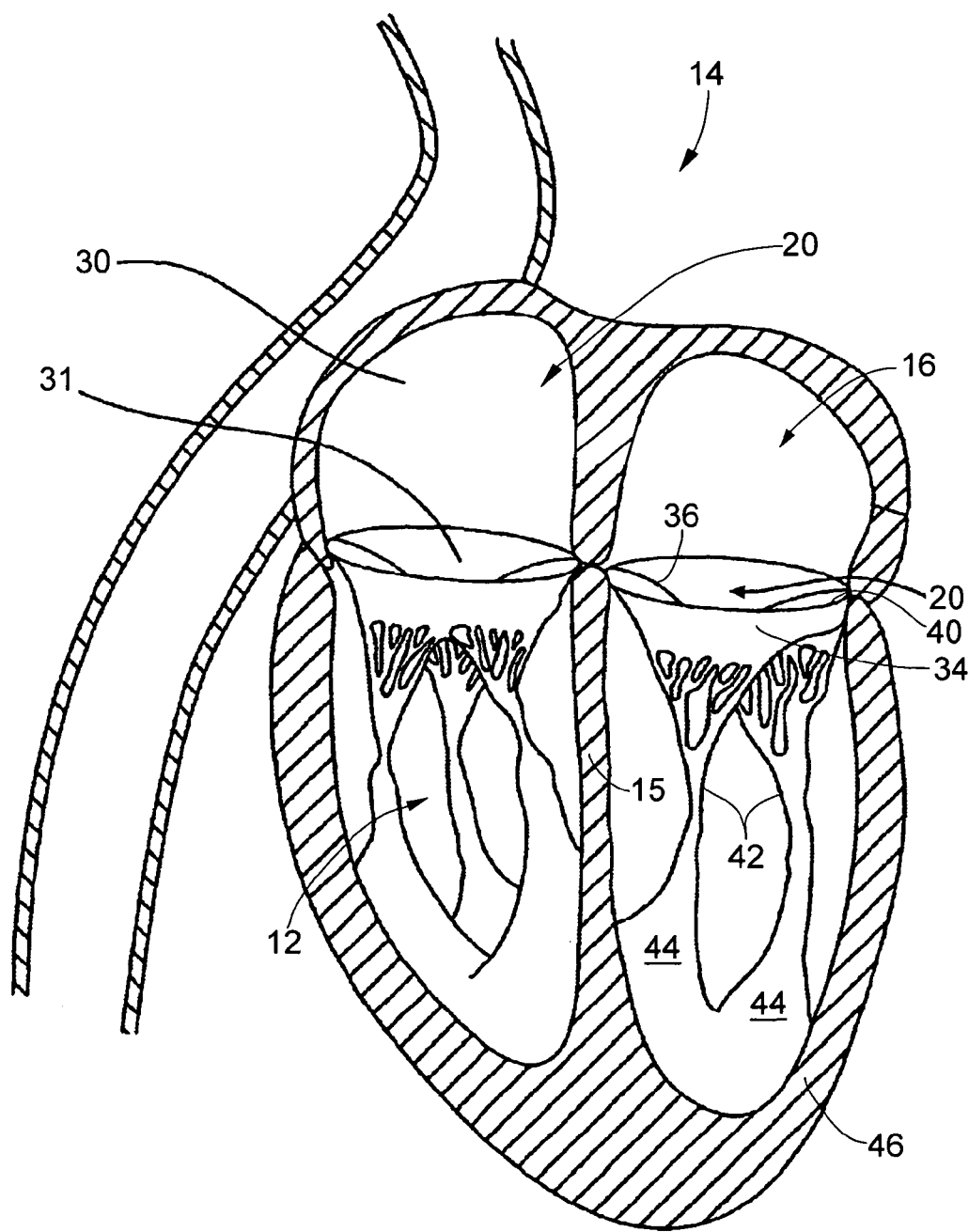
FIG. 2 is an another cross-sectional view of the heart shown in FIG. 1 during systole.

FIG. 1 is a cross-sectional view of the left and right ventricles 10 and 12, respectively, of a human heart 14 during diastole. Ventricles 10 and 12 are separated by an interatrial septum 15. FIG. 2 is a cross-sectional view of heart 14 during systole. The present invention provides methods and apparatus for the endovascular repair of cardiac valves, particularly atrioventricular valves 16, which inhibit back-flow of blood from a heart ventricle during contraction (systole). In particular, the present invention may be used in repairing, but is not limited to repairing, mitral valves 20.

As used herein, the term "endovascular," refers to procedure(s) of the present invention that are performed with interventional tools and supporting catheters and other equipment introduced to the heart chambers from the patient's arterial or venous vasculature remote from the heart. The interventional tools and other equipment may be introduced percutaneously, i.e., through an access sheath, or may be introduced via a surgical cut down, and then advanced from the remote access site through the vasculature until they reach heart 14. As such, the methods and apparatus described herein generally do not require penetrations made directly through an exterior heart muscle, i.e., myocardium, although there may be some instances where penetrations will be made interior to the heart, e.g., through the interatrial septum to provide for a desired access route. Moreover, as will be appreciated by one of ordinary skill in the art, the methods and apparatus described herein are not limited to use with percutaneous and intravascular techniques, but rather the present invention may be used with open surgical procedures as well.

The atrioventricular valves 16 are each located at a junction of the atria and their respective ventricles. The atrioventricular valve 16 extending between the right atrium 30 and the right ventricle 12 has three valve leaflets (cusps) and is referred to as the tricuspid or right atrioventricular valve 31. The atrioventricular valve 16 between the left atrium 32 and the left ventricle 10 is a bicuspid valve having only two leaflets or cusps 34 and is generally referred to as the mitral valve 20.

During operation of the heart 14, the valve leaflets 34 open during diastole when the heart atria fill with blood, allowing the blood to pass into the ventricle. During systole, however, the valve leaflets 34 are pushed together such that the free edges 36 of the leaflets 34 are closed against each other along a line of coaptation to prevent the back-flow of blood into the atria. Back flow of blood or "regurgitation" through the mitral valve 20 is facilitated to be prevented when the leaflets 34 are closed, such that the mitral valve 20 functions as a "check valve" which prevents back-flow when pressure in the left ventricle 10 is higher than that in the left atrium 32.

The mitral valve leaflets 34 are attached to the surrounding heart structure along an annular region referred to as the valve annulus 40. The free edges 36 of the leaflets 34 are secured to the lower portions of the left ventricle 10 through tendon-like tissue structures, known as chordae tendineae or chordae 42. The chordae 42 are attached to the papillary muscles 44 which extend upwardly from the lower portions of the left ventricle and interventricular septum 46.

A number of structural defects in the heart can cause mitral valve regurgitation. For example, ruptured chordae 42 may cause a valve leaflet 34 to prolapse if inadequate tension is induced to the leaflet 34 through the remaining unruptured chordae 42. Moreover, and for example, regurgitation may also occur in patients suffering from cardiomyopathy, wherein the heart 14 is dilated and the increased size prevents the valve leaflet edges 36 from contacting each other properly, or in patients who have suffered ischemic heart disease wherein the functioning of the papillary muscles 44 may be impaired. Generally during regurgitation the free edges 36 of the anterior and posterior leaflets 34 do not contact sufficiently along the line of coaptation, but rather leakage may occur through a gap defined between the leaflets 34.

Figure 3:
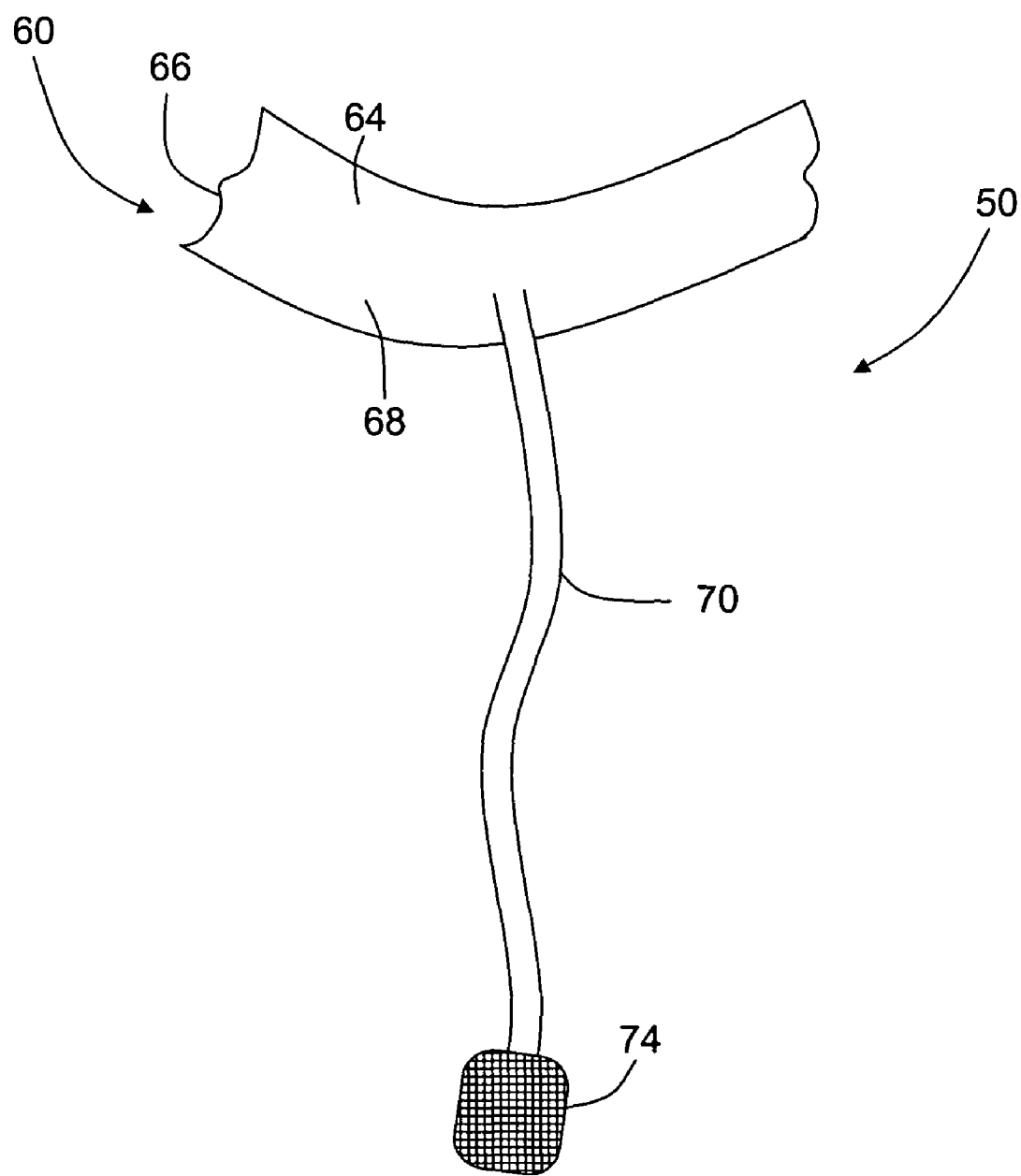
FIG. 3 is an exemplary schematic illustration of a fastening mechanism that may be used to facilitate repair of a cardiac valve within the heart shown in FIGS. 1 and 2.
Figure 4:
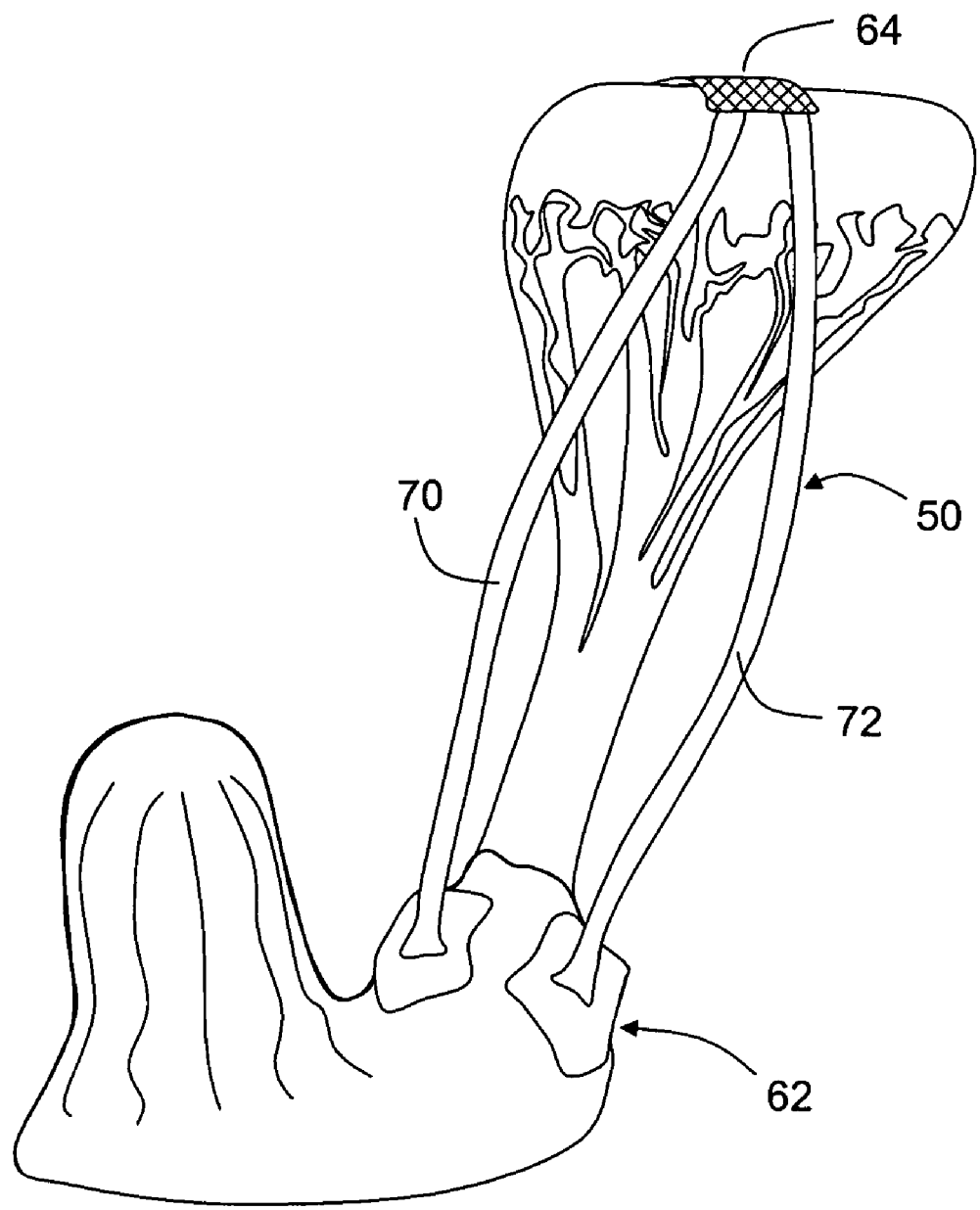
FIG. 4 is an enlarged view of a portion of the fastening mechanism shown in FIG. 3 and coupled to a papillary muscle in the heart shown in FIGS. 1 and 2.

FIG. 3 is an exemplary schematic illustration of a fastening mechanism 50 that may be used to facilitate repair of an atrioventricular valve 16 within heart 14 (shown in FIGS. 1 and 2). FIG. 4 is an enlarged view of a portion of the fastening mechanism shown in FIG. 3 and coupled to a papillary muscle 44. Fastening mechanism 50 includes a first attachment end 60 and a second attachment end 62. In the exemplary embodiment, first attachment end 60 includes a generally deformable clip portion 64 that is sized and shaped to couple to a free edge 36 (shown in FIGS. 1 and 2) of a leaflet 34 (shown in FIGS. 1 and 2). In alternative embodiments, first attachment end 60 is coupled to leaflet 34 without using clip portion 64.

Overall dimensions of, and material properties used in fabricating, clip portion 64 are variably selected based on the leaflet 34 being repaired. In the exemplary embodiment, portion 64 is pinched or crimped against a leaflet free edge 36 to facilitate repair of the valve as described in more detail below. More specifically, in this embodiment, fastening mechanism 50 is coupled to valve 16 such that an outer surface of leaflet free edge 36 is grasped without mechanism 50 penetrating the leaflet tissue. Specifically, in the exemplary embodiment, the leaflet free edge 36 is crimped between opposing sides 66 and 68 of portion 64. In another embodiment, portion 64 is coupled to a free edge 36 using any suitable means that enables portion 64 to remain coupled to leaflet free edge 36, such as, but not limited to, with gluing, stapling, suturing, fusing, riveting, external clips, or any combination thereof.

Alternatively, first attachment end 60 may be secured to leaflet 34 through atraumatic partial, or full penetration, or piercing of leaflet 34. For example, first attachment end 60 and/or portion 64 may include attachment prongs that extend from clip portion 64 and that are configured to pinch, partially penetrate, or pierce the leaflet 34. In one alternative embodiment, first attachment end 60 may be inserted from a first side of the leaflet 34, through leaflet 34, and outward from an opposite second side of the leaflet 34. In such an embodiment, in use first attachment end 60 is coupled to, and secured against the second side of the leaflet. In another alternative embodiment, first attachment end is inserted only partially through the leaflet 34, and thus is secured to leaflet tissue intermediate the first and second sides of the leaflet.

In another alternative embodiment, first attachment end 60 is attached to leaflet 34 using any suitable means that will enable fastening mechanism 50 to function as described herein, such as, but not limited to, an adhesive process, a riveting process, a suturing process, a stapling process, or any combination thereof. In a further alternative embodiment, a threaded locking member or any other suitable mechanical coupling, may be used to secure first attachment end 60 to the leaflet. In another alternative embodiment, attachment end 60 may be fused directly to the leaflet 34 using a known fusion process in which laser, RF, microwave or ultrasonic energy, for example, is applied at specified coaptation points.

In the exemplary embodiment, clip portion 64 is fabricated from a formable material that is coated in a protective cloth-like material. Clip portion 64 may be fabricated from any suitable biocompatible material that enables fastening mechanism 50 to function as described herein, such as, but not limited to, titanium alloys, platinum alloys, stainless steel, or any combination thereof. In the exemplary embodiment, clip portion 64 is coated with a fabric material such as, but not limited to, a DACRON® material, a TEFLON® material, a GORE-TEX®, or any material or combination thereof that enables clip portion 64 to function as described herein. In one embodiment, clip portion 64 is covered by a material that encourages tissue in-growth.

In the exemplary embodiment, a tensioning member 70 extends from clip portion 64 to second attachment end 62. The overall size, shape, and material used in member 70 is variably selected depending on the application. For example, in one embodiment, member 70 is fabricated from a mesh material. The relative location of member 70 with respect to clip portion 64 is variably selected based on the amount of tension to be induced, the desired locations for the tension to be induced, and based on the leaflet 34 being repaired.

In the exemplary embodiment, tensioning member 70 includes an attachment pad 74. The overall size, shape, thickness, and material used in fabricating pad 74, as well as the number and location of pad 74, are variably selected based on the intended use of fastening mechanism 50. Alternatively, fastening mechanism 50 includes more than one tensioning member 70. In another alternative embodiment, fastening mechanism 50 may include a single tensioning member 70 that includes a forked or bifurcated end that includes two pads 74. In yet another alternative embodiment, fastening tensioning member 70 does not include pad 74. In a further alternative embodiment, fastening mechanism 50 includes at least one tensioning member that is formed with a looped end that is sized to circumscribe the cardiac structure to which it is attached, and is cinchable to facilitate securing fastening mechanism 50 to the papillary muscle 44. Tensioning member 70 facilitates inducing tension to the leaflet 34 being repaired, and pad 74 facilitates distributing loading across the papillary muscle 44. Moreover, pad 74 is sized for placement along an external surface of papillary muscle 44 when fastening mechanism 50 is coupled to the papillary muscle 44.

In the exemplary embodiment, tensioning member 70 and pad 74 are formed integrally together. Alternatively, pad 74 may be securely coupled to member 70 using any of a plurality of known coupling means. In the exemplary embodiment, member 70 is coupled to papillary muscle 44 using a fastener (not shown) that is inserted at least partially through papillary muscle 44. In one embodiment, the fastener has a tack-like configuration. In another embodiment, the fastener is mechanically coupled to the papillary muscle 44 using, for example, a suitable threaded coupling. In a further embodiment, at least one of a pair of interlocking fasteners is inserted through a pad 74 prior to insertion through the papillary muscle 44 and prior to the two fasteners being interlocked. In another embodiment, pad 74 is coupled in position against the papillary muscle 44 by a cinch-type fastener that circumscribes the papillary muscle 44 when securely cinched. In another alternative embodiment, pad 74 is coupled directly to the papillary muscle 44 using any suitable means that will enable fastening mechanism 50 to function as described herein, such as, but not limited to, an adhesive process, a riveting process, a suturing process, a coil or corkscrew device, a stapling process, external clips, or any combination thereof. In a further alternative embodiment, a threaded locking member and a self-locking or spin-lock ratcheting fastener may be used to secure member 70 to the papillary muscle 44. In yet a further alternative embodiment, pad 74, and/or tensioning member 70 is coupled to the papillary muscle 44 using a flat ribbon that has been heat-set in the shape of double loops.

Pad 74 and member 70 may be fabricated from any material that enables pad 74 and member 70 to function as described herein. For example, pad 74 and member 70 may be fabricated from, but are not limited to being fabricated from, a DACRON® material, a TEFLON® material, a GORE-TEX®, or any material or combination. In addition, depending on the application, pad 74 and member 70 may be fabricated from, but are not limited to being fabricated from a superelastic material or a shaped memory alloy (SMA) material, such as, but not limited, to Nitinol®, stainless steel, plastic, or any of several known shaped memory alloys (SMA) that have properties that develop a shaped memory effect (SME). In one embodiment, pad 74 is fabricated from a material that encourages tissue in-growth.

During use, to repair a mitral valve 20 using fastening mechanism 50, first attachment end 60 is coupled securely to mitral valve 20 and second attachment end 62 is coupled to a cardiac structure, such as the papillary muscle 44. Alternatively, second attachment end 62 may be coupled to any cardiac structure other than a mitral valve leaflet 34 such as, but not limited to, a ventricular wall 46 adjacent the atrioventricular valve 30, a valve chordae 42, either intact or ruptured, a valve annulus 36, an interatrial septum 15 or any combination thereof. In the exemplary embodiment, second attachment end 62 is coupled to the papillary muscle 44. More specifically, when end 62 is firmly secured to the papillary muscle 44, pad 74 is retained tightly against the exterior surface of the papillary muscle 44. As such, loading induced to the papillary muscle from fastening mechanism 50 is distributed across pad 74.

In the exemplary embodiment, overall dimensions and material properties of member 70 are variably selected to facilitate inducing a desired tension to leaflet 34 and to facilitate improving the ability of the atrioventricular valve 16 to close against the elevated pressures within the ventricle during systole. More specifically, member 70 is variably selected to facilitate modifying operation of the leaflet 34 such that the free ends 36 of the opposed leaflets 34 again contact each other during systole along the line of coaptation to prevent the back-flow or regurgitation of blood through the mitral valve 20 into the atria.

Figure 5:
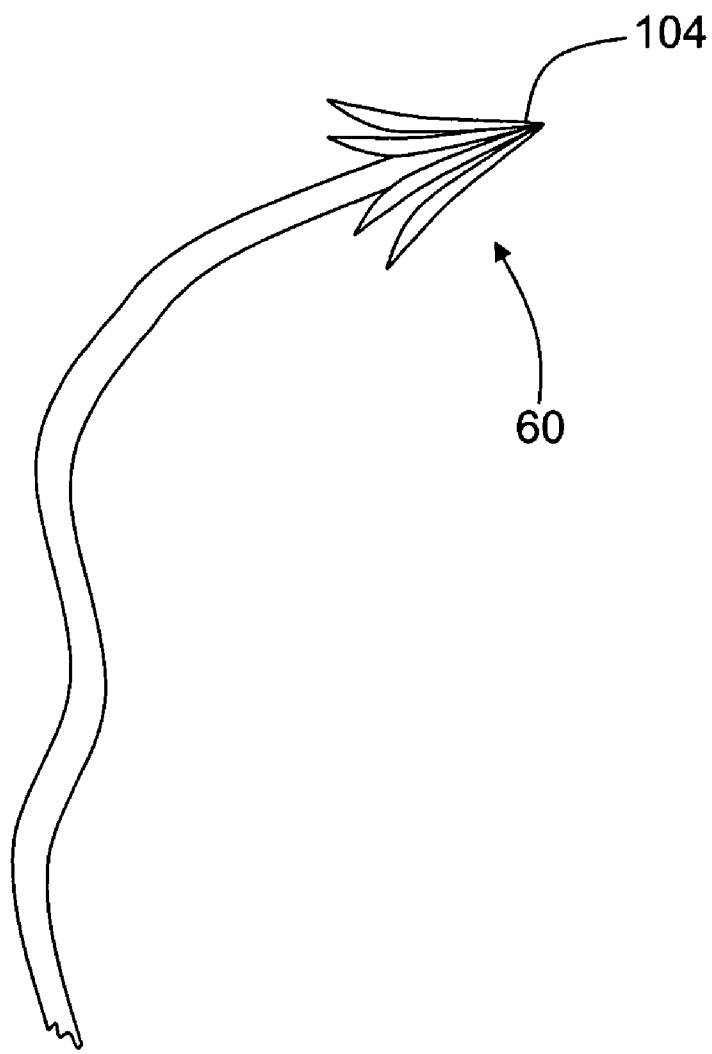
FIG. 5 is a schematic view of an alternative embodiment of a portion of a fastening mechanism that may be used to facilitate repair of a cardiac valve within the heart shown in FIGS. 1 and 2.

FIG. 5 is a schematic view of an alternative embodiment of a portion of a fastening mechanism 100 that may be used to facilitate repair of a cardiac valve 16 (shown in FIGS. 1 and 2). Fastening mechanism 100 is substantially similar to fastening mechanism 50 (shown in FIGS. 3 and 4) and, components of fastening mechanism 100 that are identical to components of fastening mechanism 50 are identified in FIG. 5 using the same reference numerals used in FIGS. 3 and 4. Accordingly, fastening mechanism 100 includes first attachment end 60, second attachment end 62 (shown in FIGS. 3 and 4), and at least one tensioning member 110 extending therebetween. In the exemplary embodiment, tensioning member 110 includes an anchor member 112. It should be noted that although attachment end 60 is illustrated, the anchor member 112 may also be included at attachment end 62 and/or end 60, or at any suitable location between ends 60 and 62 depending on the application.

Tensioning member 110 is substantially similar to tensioning member 70 and as such, facilitates inducing tension to the leaflet 34 (shown in FIGS. 1 and 2) being repaired. In the exemplary embodiment, tensioning member 110 and anchor member 112 are formed integrally together. Alternatively, anchor member 112 may be securely coupled to tensioning member 110 using any of a plurality of known coupling means. In the exemplary embodiment, member 110 is coupled to leaflet 34 using anchor member 112, or any other cardiac structure other than a mitral valve leaflet 34, such as, but not limited to, a ventricular wall 46 (shown in FIGS. 1 and 2) adjacent the atrioventricular valve 30 (shown in FIGS. 1 and 2), a valve chordae 42 (shown in FIGS. 1 and 2), either intact or ruptured, a valve annulus 36 (shown in FIGS. 1 and 2), an interatrial septum 15 (shown in FIGS. 1 and 2), a papillary muscle 44 (shown in FIGS. 1, 2, and 4), or any combination thereof.

In the exemplary embodiment, anchor member 112 has a distal end 114 that is pointed and is self-piercing that facilitates transmural attachment to a ventricular wall. Accordingly, the anchor member distal end 114 may be fabricated of any material having sufficient rigidity to pierce, and/or at least partially penetrate, through a portion of the cardiac component to which it is intended to be attached. For example, the distal end 114 may be fabricated from, but is not limited to being fabricated from, stainless steel, titanium, various shaped memory or superelastic materials, metal alloys, various polymers, and combinations thereof. Moreover, the geometries, tip sharpness, and dimensions of anchor member 112 are variably selected to ensure a desired amount of piercing, if any, occurs. In an alternative embodiment, the anchor member distal end 114 does not actually pierce the cardiac structure, but rather is positioned in a desired position by a surgical instrument, such as, but not limited to a piercing catheter or a needle.

In the exemplary embodiment, anchor member 112 includes a plurality of anchoring arms 120 that are biased outwardly from tensioning member 110. Alternatively, anchor member 112 may include, but is not limited to including, a plurality of penetrating and/or non-penetrating petals, wings, propellers, coils, arms, ribbons, tubes, loops, grappling hooks, barbs, or clips, that are extend outwardly from tensioning member 110 to enable fastening mechanism 100 to function as described herein. Moreover, in other embodiments, anchor member 112 may include expandable arms that expand outwardly from a compressed state. For example, in one embodiment, the arms 120 function similarly to an umbrella and include a pleated, supported material member that is biased outwardly, as described herein. Furthermore, the cross-sectional shape of arms 120 is illustrated as exemplary only. Rather, anchor member 112, arms 120, and tensioning member 110 may be fabricated with any cross-sectional shape that enables fastening mechanism 100 to function as described herein.

In the exemplary embodiment, arms 120 are biased outwardly such as is possible using pre-shaped, resilient metallic rods, for example. Alternatively, the arms 120 may be fabricated from any suitable material and in any suitable manner that enables arms 120 to function as described herein. For example, arms 120 may be fabricated from, but are not limited to being fabricated from Nitinol®, stainless steel, plastic, superelastic alloys, polymers, or any of several known shaped memory alloys (SMA) that have properties that develop a shaped memory effect (SME). Moreover, arms 120 may be fabricated from, but are not limited to being fabricated from, a DACRON® material, a TEFLON® material, a GORE-TEX®, or any material or combination. In one embodiment, arms 120 are fabricated from a material that encourages tissue in-growth.

During installation, after distal end 114 has penetrated at least partially through the cardiac component to which it is being attached, arms 120 are advanced through the penetration or opening and are displaced outwardly. More specifically, as tensioning member 100 is withdrawn or retracted from the opening in an opposite direction to that of insertion within the opening, because arms 120 are biased outwardly from tensioning member 100. More specifically, the biasing of the arms 120 causes the arms 120 to contact the surface of the cardiac component radially outward from the opening, such that the arms 120 are not retractable through the opening as tensioning member 100 is withdrawn from the opening. Rather, as tensioning member 100 is withdrawn from the opening, anchor member 112 is secured against a tissue surface of the cardiac component.

Figure 6:
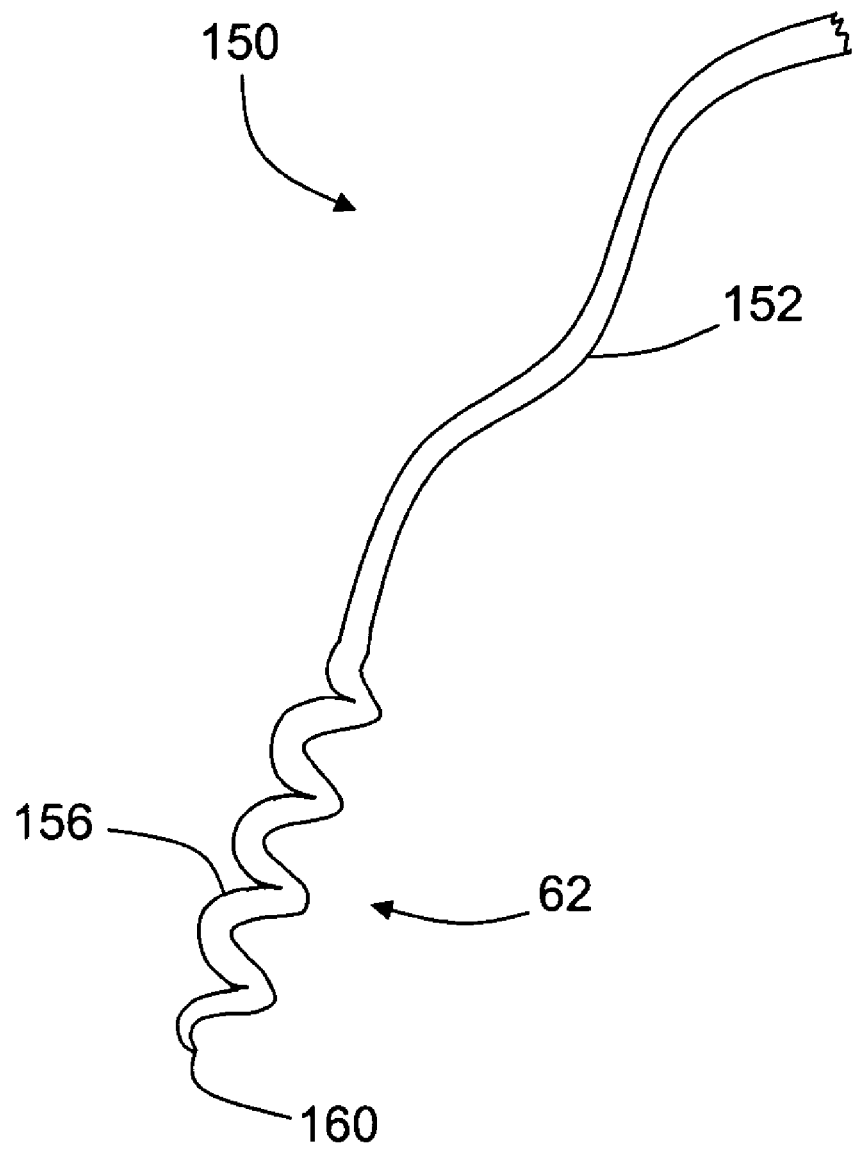
FIG. 6 is a schematic view of an another alternative embodiment of a portion of a fastening mechanism that may be used to facilitate repair of a cardiac valve within the heart shown in FIGS. 1 and 2.

FIG. 6 is a schematic view of an alternative embodiment of a portion of a fastening mechanism 150 that may be used to facilitate repair of a cardiac valve 16 (shown in FIGS. 1 and 2). Fastening mechanism 150 is substantially similar to fastening mechanisms 50 and 100 (shown in FIGS. 3 and 4, and 5, respectively) and, components of fastening mechanism 150 that are identical to components of fastening mechanism 50 and 100 are identified in FIG. 6 using the same reference numerals used in FIGS. 3-5. Accordingly, fastening mechanism 150 includes first attachment end 60 (shown in FIGS. 3-5), second attachment end 62 (shown in FIGS. 3 and 4), and at least one tensioning member 152 extending therebetween. In the exemplary embodiment, tensioning member 152 includes an anchor member 156. It should be noted that although attachment end 62 is illustrated, the anchor member 156 may also be included at attachment end 60 and/or end 62, or at any suitable location between ends 60 and 62 depending on the application.

Tensioning member 152 is substantially similar to tensioning member 70, and/or tensioning member 110, and as such, facilitates inducing tension to the leaflet 34 (shown in FIGS. 1 and 2) being repaired. In the exemplary embodiment, tensioning member 152 and anchor member 156 are formed integrally together. Alternatively, anchor member 156 may be securely coupled to tensioning member 152 using any of a plurality of known coupling means. In the exemplary embodiment, member 152 is coupled to leaflet 34 using anchor member 156, or any other cardiac structure other than a mitral valve leaflet 34, such as, but not limited to, a ventricular wall 46 (shown in FIGS. 1 and 2) adjacent the atrioventricular valve 30 (shown in FIGS. 1 and 2), a valve chordae 42 (shown in FIGS. 1 and 2), either intact or ruptured, a valve annulus 36 (shown in FIGS. 1 and 2), an interatrial septum 15 (shown in FIGS. 1 and 2), a papillary muscle 44 (shown in FIGS. 1, 2, and 4), or any combination thereof.

In the exemplary embodiment, anchor member 156 is formed with a cork-screw or coil configuration and has a distal end 160 that is pointed and is self-piercing. Accordingly, the anchor member 156 may be fabricated of any material having sufficient rigidity to pierce, and/or at least partially penetrate, through a portion of the cardiac component to which it is intended to be attached. For example, the distal end 156 may be fabricated from, but is not limited to being fabricated from, stainless steel, titanium, various shape memory or superelastic materials, metal alloys, various polymers, and combinations thereof. In an alternative embodiment, the anchor member 156 is not self-tapping, but rather is threadably coupled within a starter hole formed a surgical instrument, such as, but not limited to a piercing catheter or a needle.

In one embodiment, anchor member 156 may be formed from a shape memory wire that is annealed or heat-set in a straight configuration and then coiled. In such an embodiment, anchor member 156 may be processed to have different properties by varying the diameter and tension therein along its length. For example, when anchor member 156 is heated to a pre-determined temperature, such as with RF energy, a designated portion of anchor member 156 will become a randomly oriented mass of material having self-locking struts to prevent disentanglement. When the anchor member 156 is heated to a different pre-determined temperature, a full entanglement of occurs such that anchor member 156 is compressed together.

In an alternative embodiment, anchor member 156 includes a plurality of tines or arms that are biased outwardly from member 156, and more particularly from tip 160. In such an embodiment, the arms facilitate securing the anchor member 156 in position within the cardiac structure to which it is embedded. Moreover, in other embodiments, anchor member 156 may include expandable arms that expand outwardly from a compressed state. Alternatively, anchor member 156 may include other self-locking struts that facilitate preventing member 156 from backing out of the cardiac structure to which it is threadalby coupled. Furthermore, the cross-sectional shape of anchor member 156 is illustrated as exemplary only. Rather, anchor member 156 and tensioning member 152 may be fabricated with any cross-sectional shape, dimensions, or material that enables fastening mechanism 150 to function as described herein. For example, anchor member 156 may be formed with, but is not limited to being formed with, a self-tapping screw configuration, a mesh configuration, or with a helical configuration.

Moreover, in another embodiment, anchor member 156 is formed with a coiled configuration having a helical filament that includes a secondary helical structure that includes, for example, a plurality of loops. In such an embodiment, anchor member 156 may include an inner element fabricated from a shaped memory material and an outer element that is substantially concentrically aligned with respect to the inner element, and is fabricated from a second material, such as a radiopaque material or a heat-activated material. Furthermore, in other embodiments, to facilitate endovascular orientation, the coil may be fabricated with a stacked coil configuration in which no space is defined between adjacent windings of the coil, but rather, the coil assumes a coil configuration when heated to a pre-determined temperature as it is deployed.

Figure 7:
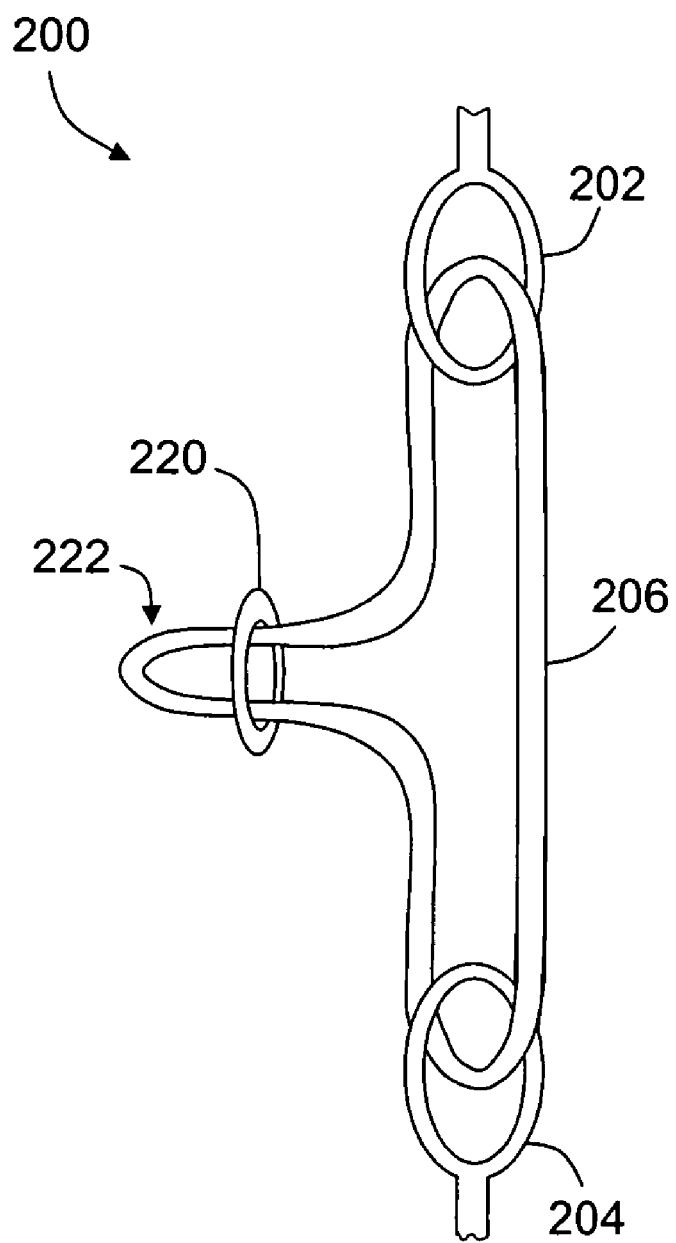
FIG. 7 is a schematic view of a further alternative embodiment of a portion of a fastening mechanism that may be used to facilitate repair of a cardiac valve within the heart shown in FIGS. 1 and 2.

FIG. 7 is a schematic view of an alternative embodiment of a portion of a tensioning member 200 that may be used to facilitate repair of a cardiac valve 16 (shown in FIGS. 1 and 2). Tensioning member 200 extends between first and second attachment ends 60 and 62 (shown in FIGS. 3 and 4) and in the exemplary embodiment, includes at least two anchoring loops 202 and 204, and an adjustment mechanism 206 extending between loops 202 and 204. In the exemplary embodiment, loops 202 and 204 are each formed integrally with respective attachment ends 60 and 62. In another embodiment, loops 202 and 204 are coupled to ends 60 and 62 using any suitable coupling means.

In the exemplary embodiment, adjustment mechanism 206 enables each attachment end 60 and 62 to be coupled to a leaflet 34 (shown in FIGS. 1 and 2) and to any other cardiac structure other than a mitral valve leaflet 34, without tension being induced to either end 60 or 62. Moreover, once ends 60 and 62 are coupled to the leaflet 34 and the cardiac structure, adjustment mechanism 206 enables a pre-determined tension to be induced between the leaflet 34 and the cardiac structure.

In the exemplary embodiment, adjustment mechanism 206 functions similarly to a drawstring and includes a locking mechanism 220 that facilitates maintaining a desired tension between the leaflet 34 and the cardiac structure. More specifically, after ends 60 and 62 have each been securely coupled to the leaflet and the cardiac structure, as adjustment loop 222 is pulled away from ends 60 and 62, adjustment mechanism 206 is drawn radially inward between ends 60 and 62, inducing tension between the leaflet 34 and the cardiac structure, and locking mechanism 220 is coupled to adjustment loop 222 to facilitate ensuring that ends 60 and 62 are maintained in their relative position such that the tension induced between ends 60 and 62 is maintained. In an alternative embodiment, adjustment mechanism 206 does not include locking mechanism 222, but rather any suitable method of maintaining the tension between ends 60 and 62 may be utilized, such as, but not limited to, self-locking twist fastener devices or swivel fasteners. Moreover, in a further embodiment, adjustment mechanism 206 does not include locking mechanism 220, but rather the tension induced by the placement of loop 222 is maintained by a knot tied in position adjacent loop 222.

In alternative embodiments, other adjustment mechanisms other than mechanism 206 may be used, such as, but not limited to, the installation of a spreader bar mechanism within at least one loop of a daisy chained tension member, the use of a turnbuckle-type mechanism, and/or the use of tensioning member that is shortened as it is twisted, such as would be possible with a tourniquet-type attachment. Moreover, in further alternative embodiments, at least a portion of adjustment mechanism 206 is fabricated from a shaped metal alloy that is formed into a component that when coupled within a fastener assembly either constricts or bows outwardly to induce tension between the ends 60 and 62.

Figure 8:
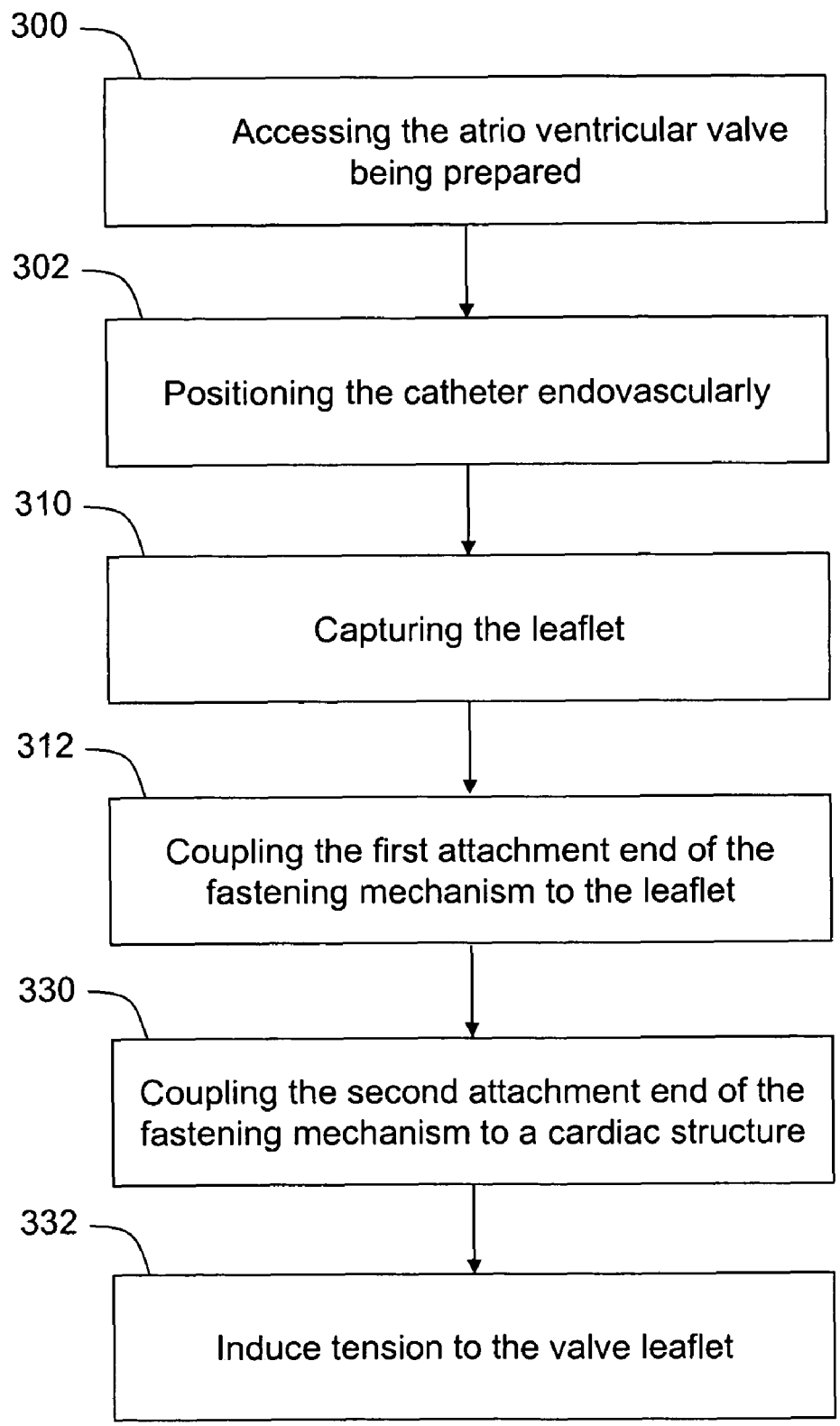
FIG. 8 is a flowchart illustrating an exemplary method for the endovascular repair of a cardiac valve.

FIG. 8 is a flowchart illustrating an exemplary method for the endovascular repair of a cardiac valve. Initially, the mitral valve, or other atrioventricular valve being repaired is accessed percutaneously 300. Depending on the point of vascular access, the approach to the mitral valve may be "antegrade" and require entry into the left atrium by crossing the interatrial septum. Alternatively, approach to the mitral valve can be "retrograde" wherein the left ventricle is entered through the aortic valve. Once access 300 is achieved, the interventional tools and supporting catheter(s) will be positioned 302 endovascularly adjacent the valve being repaired. As will be appreciated by one of ordinary skill in the art, the present invention may be used with open surgical techniques wherein the heart is stopped and the heart valve accessed through the myocardial tissue.

The interventional tools used for performing the valve repairs may be specifically designed for use with the present invention, or existing tools may be modified to accommodate the present invention. For example, in one embodiment, a 1° catheter is used to position or guide a plurality of smaller catheters in which the 1° catheter is used to accomplish general positioning of the device relative to the valve being repaired, and the smaller catheters facilitate the more precise positioning necessary to repair the valve in accordance with the present invention. In other embodiments, a guide catheter, a needle bearing catheter, an introducer, or a similar device may be used.

Once positioned 302, the leaflet to be repaired is captured 310 and the first attachment end of the fastening mechanism is securely coupled to the leaflet 312. Specifically, as described above, the fastening mechanism may be coupled to the leaflet in a plurality of manners, but in each case, the first attachment end of the mechanism is securely coupled to the valve leaflet in need of repair. The leaflet may be captured 310 using any of a plurality of known methods, including, but not limited to using grasping pins, articulated graspers, vacuum-assisted graspers, or any other suitable method.

The second attachment end of the fastening mechanism is then securely coupled 330 to a cardiac structure other than a mitral valve leaflet. The tension induced 332 to the mitral valve leaflet is selected to substantially simulate the same tension, operation, and functionality of a natural chordae member coupled to the leaflet. In at least some embodiments, tension induced to the mitral valve leaflet is adjustable via adjustments of the tensioning member.

After repairing the valve leaflet, flow through the valve can be observed by conventional cardiac imaging techniques, such as trans-esophegeal echocardiography (TEE), intracardiac echocardiography (ICE) or other ultrasonic imaging technique, fluoroscopy, angioscopy, catheter based magnetic resonance imaging (MRI), computed tomography (CT) and the like. By observing the flow through the repaired valves, it can be determined whether or not back flow or regurgitation has ceased, or whether the tension induced to the leaflet requires adjustment.

Exemplary embodiments of methods and fastener mechanisms for use in repairing atrioventricular valves are described above in detail. Although the methods are herein described and illustrated in association with the above-described atrioventricular valve, it should be understood that the present invention may be used with any atrioventricular valve. More specifically, the fastener mechanisms and methods of repair are not limited to the specific embodiments described herein, but rather, aspects of each fastener mechanism and/or method of repair may be utilized independently and separately from other fastener mechanisms and/or repair methods.

While the invention has been described in terms of various specific embodiments, those skilled in the art will recognize that the invention can be practiced with modification within the spirit and scope of the claims.

What is claimed is:

1. A method of repairing a mitral valve in the heart of a patient by correcting an insufficiency of a valve leaflet of the mitral valve, wherein the valve is connected to at least one natural chordae, said method comprising:
   accessing the patient's mitral valve via at least one of a guide catheter and an interventional tool;
   securing a first end of a fastening mechanism positioned in the heart by the at least one of a guide catheter and an interventional tool to the valve leaflet; and
   coupling a second end of the fastening mechanism within a left ventricle of the heart to a cardiac structure other than the mitral valve leaflet such that the fastening mechanism simulates the function of a natural chordae, wherein said method is performed without penetrating through a myocardium, and wherein the at least one of a guide catheter and an interventional tool is removed from the heart such that the fastening mechanism remains coupled to the valve leaflet and the cardiac structure.

2. The method in accordance with claim 1 wherein securing a first end of a fastening mechanism to the valve leaflet further comprises securing the first and second ends of the fastening mechanism within the patient while the patient's heart is non-arrested.

3. The method in accordance with claim 1 wherein securing a first end of the fastening mechanism to the valve leaflet further comprises securing the fastening mechanism first end to an edge of the mitral valve leaflet to facilitate reducing leakage through the patient's mitral valve.

4. The method in accordance with claim 1 wherein securing a first end of the fastening mechanism to the valve leaflet further comprises inserting the first end of the fastening mechanism through an opening extending at least partially through the mitral valve leaflet.

5. The method in accordance with claim 1 wherein securing a first end of the fastening mechanism to the valve leaflet further comprises fusing the first end of the fastening mechanism to the mitral valve leaflet.

6. The method in accordance with claim 1 wherein securing a first end of the fastening mechanism to the valve leaflet further comprises:
   inserting the fastening mechanism from a first side of the mitral valve leaflet through an opening extending through the mitral valve leaflet; and
   securing the fastening mechanism to the second side of the mitral valve leaflet.

7. The method in accordance with claim 1 wherein securing a first end of the fastening mechanism to the valve leaflet further comprises securing the first end of the fastening mechanism to the mitral valve leaflet using at least one of stapling, riveting, fusing, gluing, and suturing.

8. The method in accordance with claim 1 wherein coupling a second end of the fastening mechanism to a cardiac structure other than the mitral valve leaflet further comprises securing the second end of the fastening mechanism through an opening formed in a papillary muscle.

9. The method in accordance with claim 1 wherein coupling a second end of the fastening mechanism to a cardiac structure other than the mitral valve leaflet further comprises inserting the second end of the fastening mechanism into an opening extending at least partially through at least one of a ventricular wall adjacent the atrioventricular valve, a valve chordae, a papillary muscle, and a valve annulus.

10. The method in accordance with claim 1 wherein coupling a second end of the fastening mechanism to a cardiac structure other than the mitral valve leaflet further comprises coupling the second end of the fastening mechanism to the cardiac structure using at least one of stapling, riveting, fusing, gluing, and suturing.

11. The method in accordance with claim 1 wherein coupling a second end of the fastening mechanism to a cardiac structure other than the mitral valve leaflet further comprises fusing the second end of the fastening mechanism to the cardiac structure.

12. The method in accordance with claim 1 wherein coupling a second end of the fastening mechanism to a cardiac structure other than the mitral valve leaflet further comprises threadably coupling the second end of the fastening mechanism to the cardiac structure.

13. A method of enhancing the operation of a valve leaflet in a patient's heart valve by correcting an insufficiency of the valve leaflet, said method comprising:
   inserting a guide catheter through one of the venous and arterial systems of the patient to approach the heart valve;
   guiding a fastening mechanism through the guide catheter towards the patient's heart;
   securely coupling a first end of the fastening mechanism to the valve leaflet using one of fusing, gluing, stapling, clipping, riveting, anchoring, and suturing; securely coupling, after the first end is securely coupled to the valve leaflet, a second end of the fastening mechanism within a corresponding ventricle of the heart to a cardiac structure other than the valve leaflet to facilitate enhancing operation of the heart valve, wherein said method is performed without penetrating through a myocardium; and removing the guide catheter from the patient's heart after the fastening mechanism is securely coupled to the valve leaflet and to the cardiac structure, such that the fastening mechanism remains coupled within the patient's heart and simulates the function of a native chordae.

14. The method in accordance with claim 13 wherein securing a second end of the fastening mechanism further comprises securing the second end to the cardiac structure using one of fusing, gluing, stapling, clipping, riveting, and suturing.

15. The method in accordance with claim 13 further comprising deploying a shaped memory fastener to effect securing the fastening mechanism to the valve.

16. The method in accordance with claim 13 wherein securing a second end of the fastening mechanism to a cardiac structure further comprises securing the second end of the fastening mechanism through an opening defined in the cardiac structure to which the second end is secured.

17. The method in accordance with claim 13 wherein securing a second end of the fastening mechanism to a cardiac structure comprises threadably coupling the fastening mechanism second end to the cardiac structure.

18. A method of repairing an atrioventricular valve in a patient by correcting an insufficiency of a valve leaflet of the atrioventricular valve, said method comprising:

accessing the patient's atrioventricular valve using at least one of a guide catheter and an interventional tool;

securing a fastening mechanism positioned by the at least one of a guide catheter and an interventional tool to the valve leaflet;

coupling the fastening mechanism, while the patient's heart remains beating, to at least one of a ventricular wall adjacent the atrioventricular valve, a papillary muscle, and a valve annulus to facilitate reducing leakage through the atrioventricular valve, wherein said method is performed without penetrating through a myocardium, and wherein the fastening mechanism is secured to the valve leaflet prior to being secured to at least one of a ventricular wall adjacent the atrioventricular valve, a papillary muscle, and a valve annulus; and removing the at least one of a guide catheter and an interventional tool from the patient such that the fastening mechanism remains securely coupled to the valve leaflet and to at least one of a ventricular wall adjacent the atrioventricular valve, a papillary muscle, and a valve annulus, such that the fastening mechanism simulates the function of a native chordae.

19. The method in accordance with claim 18 wherein securing a fastening mechanism to the valve leaflet further comprises securing the fastening mechanism to an edge of the valve leaflet.

20. The method in accordance with claim 18 wherein securing a fastening mechanism to the valve leaflet further comprises:

forming an opening extending at least partially through the valve leaflet; and inserting the fastening mechanism through the opening defined in the valve leaflet prior to coupling the fastening mechanism to the valve leaflet.

21. The method in accordance with claim 18 wherein securing a fastening mechanism to the valve leaflet further comprises securing the fastening mechanism to the valve leaflet using at least one of a staple, a rivet, an adhesive material, and a suture.

22. The method in accordance with claim 18 wherein securing a fastening mechanism to the leaflet further comprises securing the fastening mechanism to the valve leaflet of one of a tricuspid valve and a mitral valve.

23. The method in accordance with claim 18 wherein coupling the valve leaflet further comprises inserting a portion of the fastening mechanism at least partially through a portion of at least one papillary muscle.

24. The method in accordance with claim 18 wherein coupling the valve leaflet further comprises:

forming an opening extending at least partially through at least one of the ventricular wall adjacent the atrioventricular valve, the papillary muscle, and the valve annulus; and securing the fastening mechanism to at least one of at least one valve chordae, and the valve annulus.

25. The method in accordance with claim 18 wherein coupling the valve leaflet further comprises securing the fastening mechanism to at least one of the ventricular wall adjacent the atrioventricular valve, the papillary muscle, at least one valve chordae, and the valve annulus using at least one of a staple, a rivet, an adhesive material, and a suture.

26. The method in accordance with claim 18 wherein coupling the valve leaflet further comprises threadably coupling the fastening mechanism to at least one of the ventricular wall adjacent the atrioventricular valve, the papillary muscle, at least one valve chordae, and the valve annulus.

27. The method in accordance with claim 18 wherein securing a fastening mechanism to the valve leaflet comprises securing a fastening mechanism fabricated from at least one of a superelastic material, and a shaped memory alloy material.

* * * * *